(12) United States Patent
Martina

(10) Patent No.: US 10,201,404 B2
(45) Date of Patent: Feb. 12, 2019

(54) IMPLANT FOR DENTAL PROSTHESES

(71) Applicant: Sweden & Martina SpA, Due Carrare (PD) (IT)

(72) Inventor: Alberto Martina, Due Carrare (IT)

(*) Notice: Subject to any disclaimer, the term of this patent is extended or adjusted under 35 U.S.C. 154(b) by 0 days.

(21) Appl. No.: 15/550,790

(22) PCT Filed: Feb. 20, 2015

(86) PCT No.: PCT/IB2015/051303
§ 371 (c)(1),
(2) Date: Aug. 13, 2017

(87) PCT Pub. No.: WO2016/132178
PCT Pub. Date: Aug. 25, 2016

(65) Prior Publication Data
US 2018/0042703 A1 Feb. 15, 2018

(30) Foreign Application Priority Data

Feb. 16, 2015 (IT) .............................. PD2015A0040

(51) Int. Cl.
*A61C 8/00* (2006.01)
(52) U.S. Cl.
CPC .......... *A61C 8/0072* (2013.01); *A61C 8/0057* (2013.01); *A61C 8/0074* (2013.01); *A61C 8/0078* (2013.01); *A61C 8/0022* (2013.01)
(58) Field of Classification Search
CPC ... A61C 8/0072; A61C 8/0074; A61C 8/0022; A61C 8/0057; A61C 8/0075
See application file for complete search history.

(56) References Cited

U.S. PATENT DOCUMENTS

| 4,215,986 | A | | 8/1980 | Riess | |
|---|---|---|---|---|---|
| 5,073,111 | A | * | 12/1991 | Daftary | A61C 8/005 433/173 |
| 5,447,434 | A | * | 9/1995 | Shaw | A61C 8/005 403/285 |
| 6,109,919 | A | * | 8/2000 | Hansson | A61C 8/005 433/173 |
| 6,315,563 | B1 | * | 11/2001 | Sager | A61C 8/005 433/169 |
| 6,375,464 | B1 | | 4/2002 | Hollander | |
| 8,951,044 | B2 | * | 2/2015 | Kikuchi | A61C 13/235 433/189 |
| 9,925,024 | B2 | * | 3/2018 | Bellanca | A61C 8/0089 |
| 2013/0323678 | A1 | * | 12/2013 | Towse | A61C 8/0006 433/173 |
| 2017/0020635 | A1 | * | 1/2017 | Svoboda | A61C 8/0022 |

* cited by examiner

*Primary Examiner* — Cris L Rodriguez
*Assistant Examiner* — Hao D Mai
(74) *Attorney, Agent, or Firm* — Themis Law

(57) ABSTRACT

An implant for dental prostheses includes an endosseous portion and a stump. The endosseous portion includes a crown margin configured to be opposed to a corresponding crown margin of the stump. At least one of the crown margins is conical or however has a different taper with respect to the opposed crown margin so that, once the stump has been coupled to the endosseous portion, the contact and interference surface between the crown margins is a reduced annular surface.

6 Claims, 7 Drawing Sheets

IMPLANT FOR DENTAL PROSTHESES

The present patent concerns implants for dental prostheses and in particular it concerns a new implant for dental prostheses with an improved joint between the endosseous portion and the stump.

Implants for fixing dental prostheses are known, which comprise an endosseous portion provided with an external thread and suited to be screwed into the bone site of the dental arch, as well as a stump suited to be fixed to said endosseous portion and used for anchoring the dental prosthesis.

In order to allow the coupling to be obtained, said stump comprises a grafting appendage suited to be inserted in a corresponding grafting recess created in the endosseous portion.

In order to fix the stump to the endosseous portion in a stable manner, stumps are used which are axially hollow in order to allow the insertion of a screw that is screwed into the internally threaded recess provided in said endosseous portion.

The technique is also known according to which the stump is fixed to the endosseous portion through a cementing process, which however does not avoid the risk of possible infiltrations and furthermore may cause some inconveniences, for example the cement may come off.

Implants are also known in which the stump comprises a grafting appendage suited to become engaged in a corresponding grafting recess created in the endosseous portion, wherein said grafting appendage, for example, is threaded so that it can be screwed into said correspondingly threaded recess created in the endosseous portion.

Other improved joining methods are known like, for example, special configurations of the grafting appendages of the stump and of the recess created in the endosseous portion. For example, endosseous portions are known which are provided with an annular cavity on the opening of said recess, said cavity being suitable for the axial insertion of a corresponding annular projection present on said appendage of the stump. Endosseous portions are also known that, vice versa, are provided with an annular projection on the opening of the recess, suited to be inserted in a corresponding annular seat obtained in said appendage of the stump.

The actual sealing of the joint between the stump and the endosseous portion takes place along the opposed crown margins of the stump and of the endosseous portion, which are tightened to each other by screwing the stump.

Said system of cavities and annular projections is useful also to guide the correct positioning of the stump. In addition to the above, said system of cavities and annular projections contributes to limiting the infiltrations between the endosseous portion and the stump.

However, said infiltrations are not completely avoided, with the risk of infections or damage to the prosthetic implant.

In order to limit said infiltrations as much as possible, procedures are known for plasma sealing the joint between the endosseous portion and the stump, intended to seal said joint.

Endosseous implants are also known, in which the crown margins of the stump and/or of the endosseous portion, intended to be opposed and tightened to each other, are curved or shaped in various ways, in such a way that the contact and interference surface between said crown margins is reduced compared to the size of the crown margins themselves.

Said contact surface, for example, is an annular line or portion. Reducing the overall interference and contact surface between the stump and the endosseous portion means maximizing the tightening force exerted through the screwing operation.

The creation of said curved or shaped crown margins is very difficult and furthermore it often leads to imprecise results.

In the case where the crown margins are imprecise, there is the risk of obtaining joints that are not completely and effectively sealed.

The subject of the present invention is a new type of implant for dental prostheses, with an improved joint between the endosseous portion and the stump.

It is the main object of the present invention to guarantee optimal sealing of the joint between the endosseous portion and the stump, thus optimising and sizing exactly the contact surface between the stump and the endosseous portion, for the purpose of concentrating and therefore maximizing the tightening force.

It is another object of the present invention to provide an implant shaped in such a way as to guarantee exact and precise results.

It is another object of the present invention to improve the efficiency of the plasma sealing operations.

The new implant for dental prostheses comprises in its main parts:
  at least one endosseous portion intended to be implanted in the bone site of the dental arch, comprising at least one axial recess for grafting at least one stump, and at least one coupling crown margin;
  at least one stump suited to be fixed to said endosseous portion and used for anchoring the dental prosthesis, said stump comprising at least one grafting appendage suited to be coupled with said grafting recess of said endosseous portion, and at least one coupling crown margin suited to be opposed to said crown margin of said endosseous portion,
and wherein each one of said opposed crown margins lies on a straight or conical surface, said surfaces not being parallel to each other, so that the contact and interference surface between said crown margins is reduced compared to the size of the crown margins themselves and is near to the external edge of said crown margin of the stump.

In particular, at least one of said crown margins of said stump or of said endosseous portion is substantially in the shape of an annular truncated cone, while the other crown margin is substantially in the shape of an annular truncated cone with different taper, or planar and straight.

In this way, the contact and interference surface between said crown margins of said stump and of said endosseous portion is annular and substantially at the level of the external edge of said crown margin of the stump.

The fact that both of said crown margins lie on planar, conical or straight surfaces guarantees high precision in the production of the crown margins, making the successive sealing of the joint between the stump and the endosseous portion more efficient.

Moreover, the crown margin of the stump is smaller than the crown margin for said endosseous portion, so that the external edge of the crown margin of the stump is recessed with respect to the external edge of the crown margin of the endosseous portion.

In particular, said crown margins of said stump and of said endosseous portion have generically different taper.

In a possible solution, said crown margin of said stump is in the shape of a truncated cone, that is, it lies on a conical surface that preferably widens downwards. In this solution, the annular surface of interference with the crown margin of the endosseous portion substantially coincides with the external edge of the crown margin of the stump, which is lowered.

In this case, the crown margin of the endosseous portion can be planar, meaning that it lies on a straight plane, with no taper, or even conical, with different or preferably opposite taper with respect to that of said crown margin of the stump.

In an alternative solution, said crown margin of said endosseous portion is conical, that it, it lies on a conical surface that widens upwards.

In this solution, the annular interference surface substantially coincides with the external edge of the crown margin of the stump.

In this case, the crown margin of the stump can be planar, that is, it can lie on a straight plane, with no taper, or in turn it can be conical, too, with taper that is different or preferably opposite that of said crown margin of the endosseous portion.

In the preferred solution, the taper of said crown margin of the endosseous portion is opposite with respect to that of the crown margin of the stump, so that the annular interference surface is ideally reduced to a circular line, substantially coinciding with the external edge of said crown margin of the stump. In this way the tightening force is maximized, thus making the successive plasma sealing of the joint more effective.

The characteristics of the new implant will be highlighted in greater detail in the following description with reference to the attached drawings which are enclosed by way of non-limiting example.

FIG. 2a shows a detail of the sealing area (5) between the stump (3) and the endosseous portion (2) in a first embodiment, while

FIG. 3a shows a detail of the sealing area (5) between the stump (3) and the endosseous portion (2) in a second embodiment, while

FIG. 4a shows a detail of the sealing area (5) between the stump (3) and the endosseous portion (2) in the embodiment with direct screwing, while

Figures 1A, 1B:
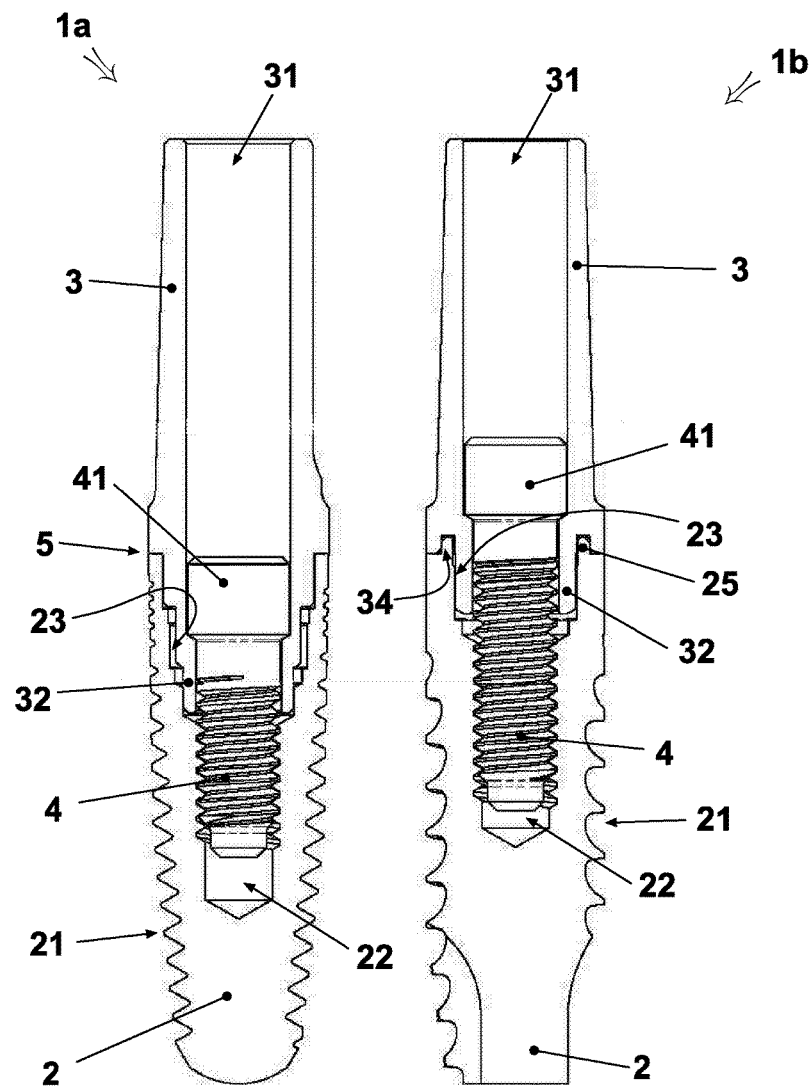
FIGS. 1a and 1b show the sectional views of two examples of the new implant for dental prostheses (1a, 1b) in two possible embodiments.

The new dental implant (1a, 1b, 1c) comprises in its main parts an endosseous portion (2) and a stump (3).

Said endosseous portion (2) is suited to be implanted in the bone site of the gum, and comprises an external thread (21) for screwing into the bone site, and an axial hole (22), preferably at least partially threaded, for grafting and tightening said stump (3).

Said stump (3) is suited to be fixed to said endosseous portion and in turn is used to fix the dental prosthesis.

Said stump (3) comprises a grafting appendage (32) suited to be inserted in a corresponding axial recess (23) shaped in said axial hole (22) of the endosseous portion (2).

In the embodiments illustrated in FIGS. 1a and 1b, said stump (3) comprises also a through axial hole (31) for the insertion of a tightening means or screw (4) suited to be screwed in said internally threaded axial hole (22) of the endosseous portion (2).

Said screw (4) comprises a head (41) suited to be used by the operator to screw and tighten said stump (3) on said endosseous portion (2).

Figure 1C:
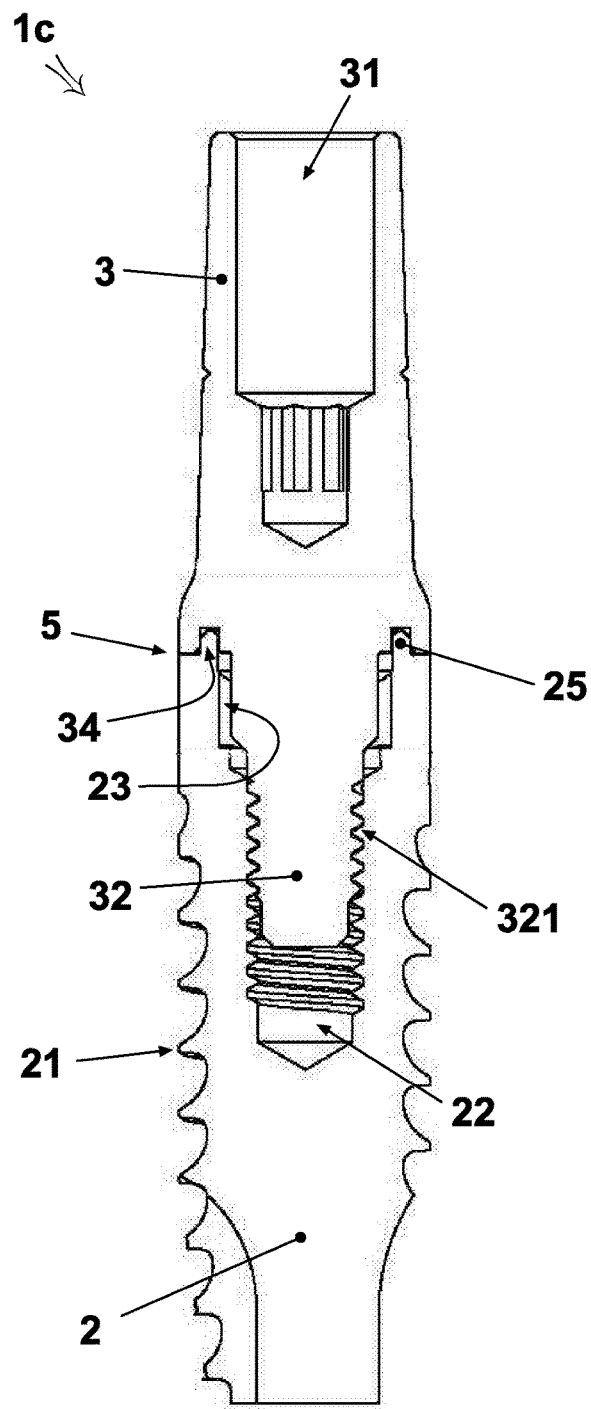
FIG. 1c shows a sectional view of a further example of the new implant (1c) with a stump (3) that can be directly screwed in the endosseous portion (2).

In the embodiment illustrated in FIG. 1c, the outside of said grafting appendage (32) of the stump (3) is at least partially threaded (321) so that it can be directly screwed into said correspondingly threaded axial hole (22) of said endosseous portion (2).

Said endosseous portion (2) comprises a crown margin (24) suited to be opposed to a corresponding crown margin (33) of said stump (3), thus defining a sealing area (5).

Figure 6:
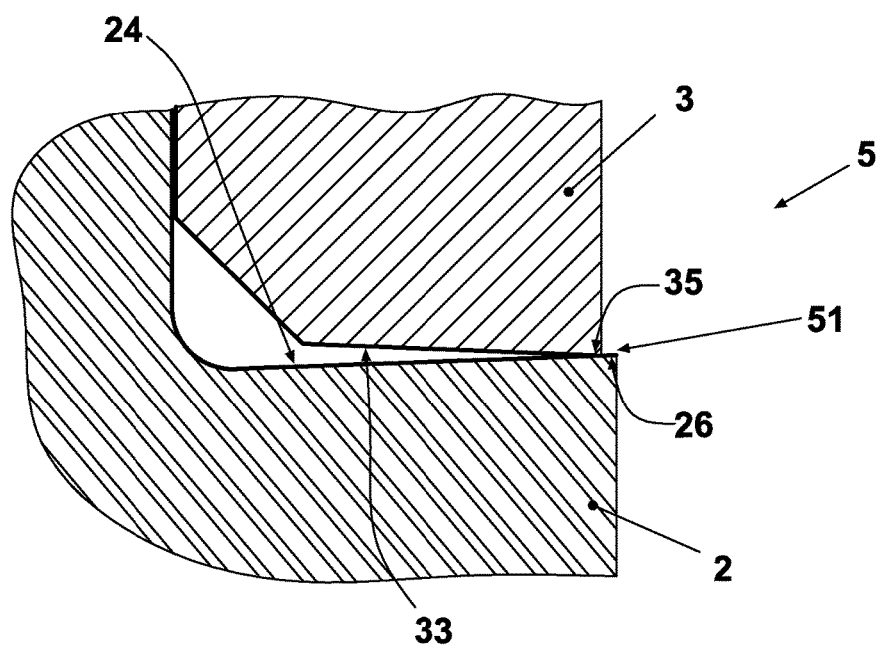
FIG. 6 shows in detail how the maximum diameter of the crown margin (33) of the stump is shorter than the maximum diameter of the crown margin (24) of the endosseous portion (2).

Said crown margin (33) of the stump (3) is conveniently smaller than said crown margin (24) of the endosseous portion (2), that is, the most external edge (35) of the crown margin (33) of the stump (3) is recessed with respect to the most external edge (26) of the crown margin (24) of the endosseous portion, as shown in FIG. 6, in which the inclination angles of the crown margins (33, 24) are enlarged for explanation purposes.

In all of the solutions described below said crown margins (33, 24) of the stump (3) and of the endosseous portion (2) lie on planar surfaces, of which at least one surface is conical, while the other surface is conical or planar and straight.

FIG. 1a shows a first embodiment of the new dental implant (1a).

In the solution illustrated in FIGS. 1b and 1c, the new dental implant (1b, 1c) is shaped in a different way, as described here below. Said endosseous portion (2) comprises an annular collar or projection (25) in proximity to the opening of said grafting recess (23) for the appendage (32) of the stump (3).

In a corresponding position on said appendage (32), said stump (3) comprises an annular seat (34) suitable for the insertion of said annular projection (25) of the endosseous portion (2).

Said annular projection (25) of the endosseous portion (2) and said annular seat (34) of the stump (3) are externally delimited by said crown margins (24, 33).

Said crown margin (33) of the stump (3) and said crown margin (24) of the endosseous portion (2) have different taper, meaning that once said stump (3) has been grafted in said endosseous portion (2) the contact and interference surface (51) between said crown margins (33, 24) is a reduced annular surface compared to the size of the crown margins (33, 24) themselves.

In particular, the two opposed margins (33, 24) are two non-parallel surfaces and the angle defined between them is preferably a 1-5° angle.

Figure 2A:
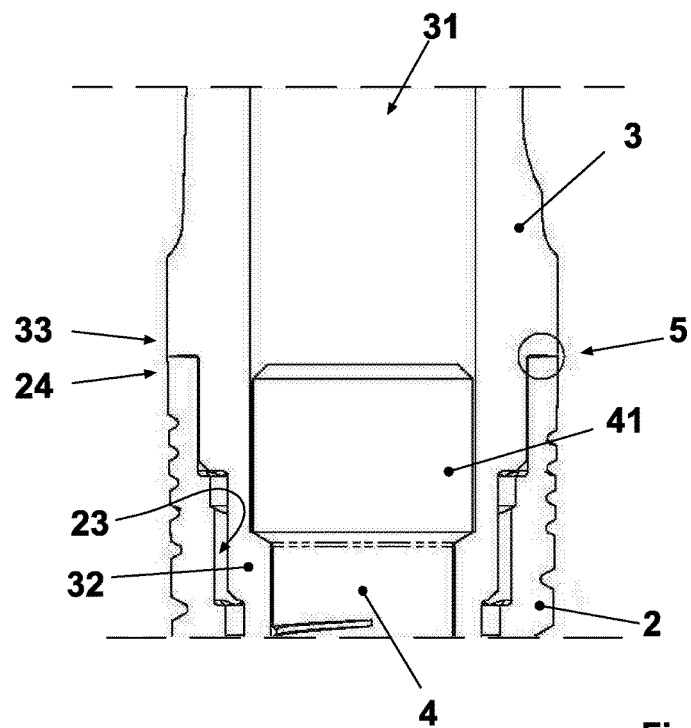
Figure 2B:
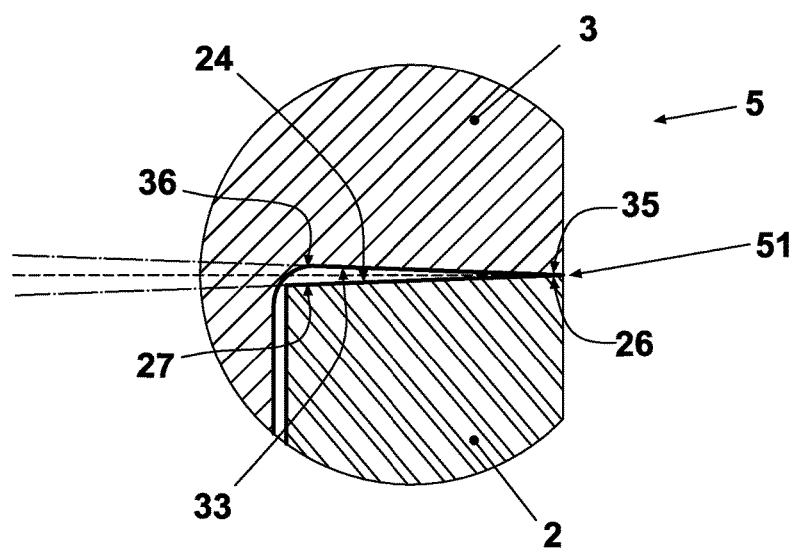
FIG. 2b shows a further enlarged detail of the non-parallel conical crown margins (33, 24) that provide the coupling between the stump (3) and the endosseous portion (2).
Figure 3A:
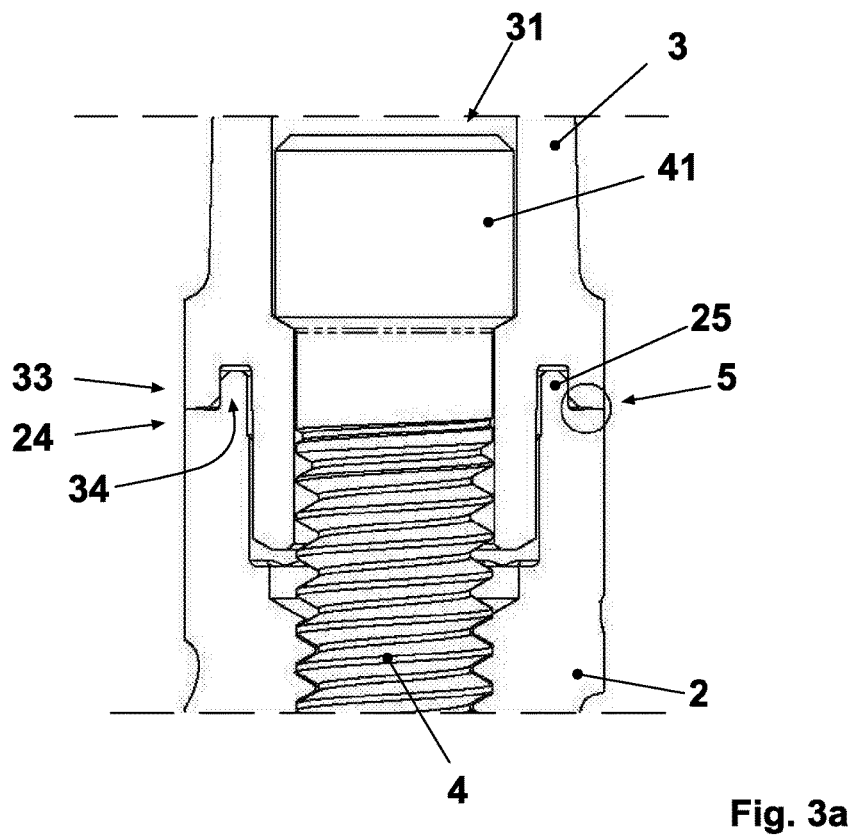
Figure 3B:
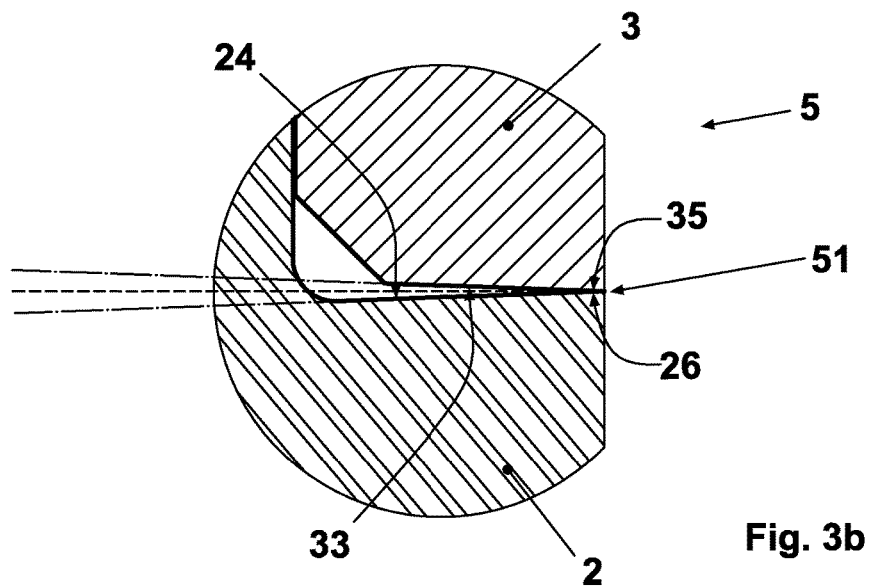
FIG. 3b shows a further enlarged detail of the non-parallel conical crown margins (33, 24) that provide the coupling between the stump (3) and the endosseous portion (2).
Figure 4A:
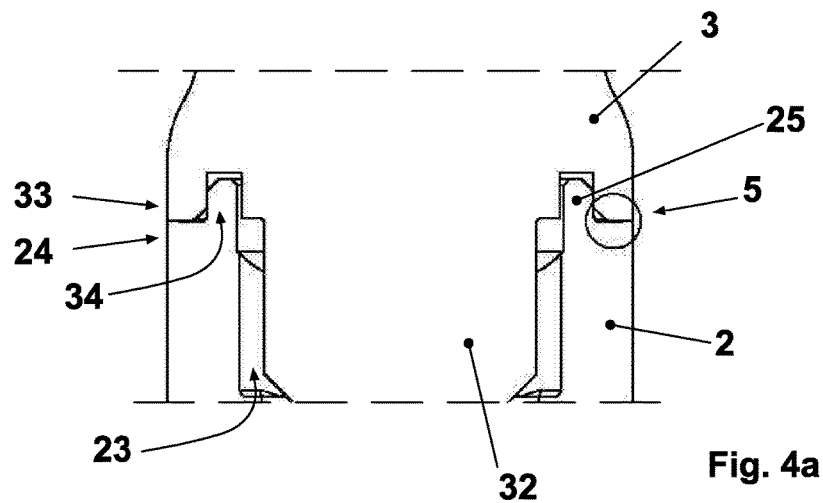
Figure 4B:
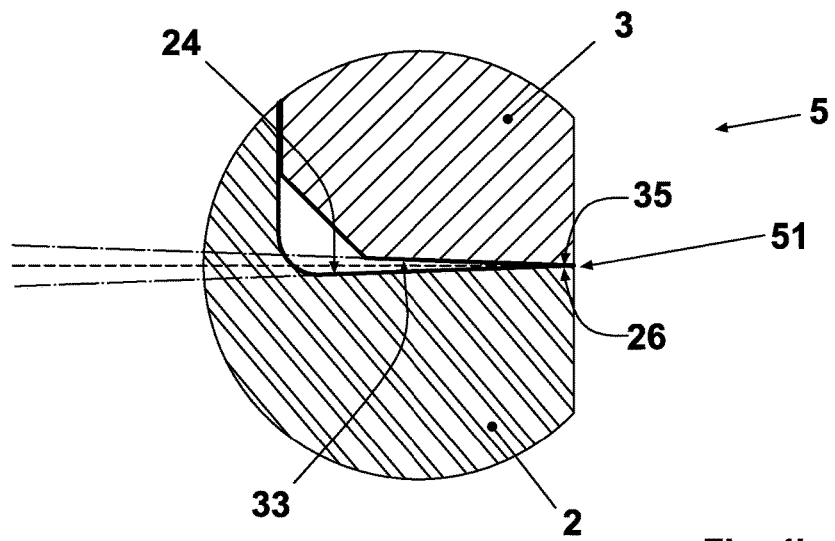
FIG. 4b shows a further enlarged detail of the conical crown margins (33, 24) that provide the coupling between the stump (3) and the endosseous portion (2).

In the solution represented in FIGS. 2b, 3b and 4b, said crown margin (33) of the stump (3) is conical, meaning that it lies on a conical surface that widens downwards, so that the external edge (35) of the crown margin (33) itself is lowered with respect to the internal edge (36).

On the contrary, the taper of said crown margin (24) of the endosseous portion (2) is opposite with respect to that of said crown margin (33) of the stump (3), that is, it lies on a conical surface that widens upwards, so that the external edge (26) of the crown margin (24) itself is raised with respect to the internal edge (27).

When said stump (3) is grafted in said endosseous portion (2), the contact and interference surface (51) of the two opposed crown margins (33, 24) is substantially circular, ideally a circular line near to or coinciding with the external edge (26, 35) of the crown margins (33, 24).

Figure 5A:
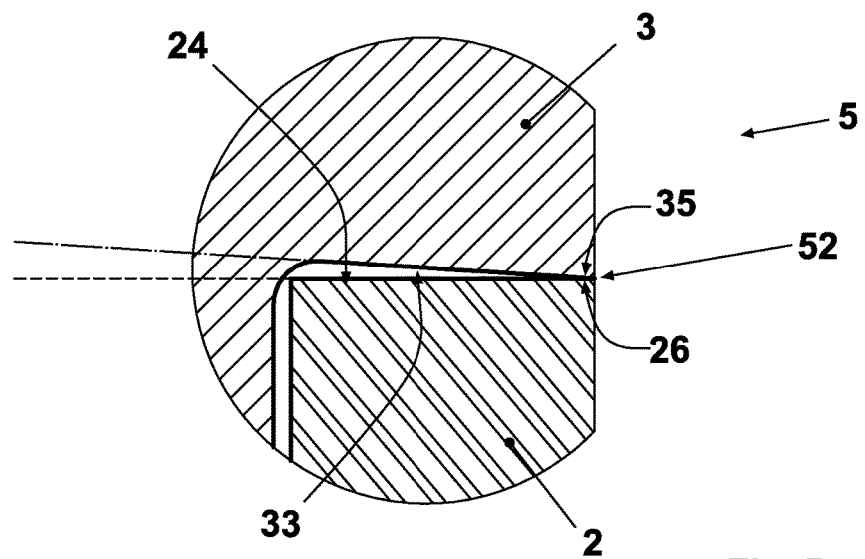
FIGS. 5a and 5b show in detail two further possible embodiments of the crown margins (33, 24).

According to a possible alternative solution schematically shown in FIG. 5a, said crown margin (33) of the stump (3) is conical, while said crown margin (24) of the endosseous portion (2) lies on a straight plane. In this case, the contact and interference surface (52) of the two opposed crown margins (33, 24) is substantially circular, ideally a circular line near to or coinciding with the external edge (26, 35) of the crown margins (33, 24).

Figure 5B:
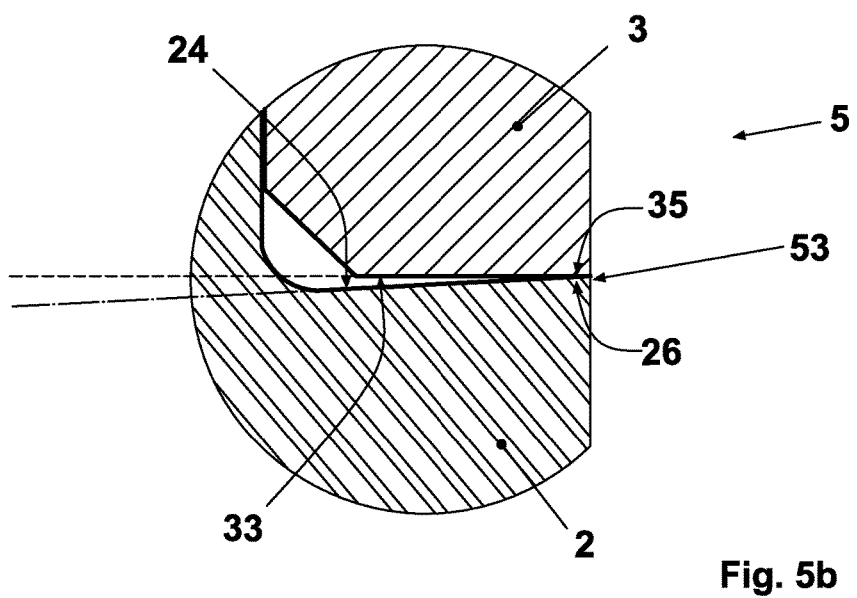

According to a possible alternative solution schematically shown in FIG. 5b, said crown margin (24) of the endosseous portion (2) is conical, while said crown margin (33) of the stump (3) lies on a straight plane. In this case, the contact and interference surface (53) of the two opposed crown margins (33, 24) is substantially circular, ideally a circular line near to or coinciding with the external edge (26, 35) of the crown margins (33, 24).

These are the schematic outlines that are sufficient for the expert in the art to implement the invention, therefore, during production variants may be developed that do not affect the substance of the innovative concept disclosed herein.

Therefore, with reference to the description provided above and the attached drawings, the following claims are expressed.

The invention claimed is:

1. An implant (1a, 1b, 1c) for dental prostheses, comprising:
    an endosseous portion (2) configured to be implanted in a bone site of a dental arch; and
    a stump (3) configured to be fixed to said endosseous portion (2) and to be coupled to a dental prosthesis,
    wherein said endosseous portion (2) comprises a crown margin (24) suited to be opposed to a corresponding crown margin (33) of said stump (3), thereby defining a sealing area (5),
    wherein said crown margin (33) of the stump (3) is opposed to and smaller than said crown margin (24) of the endosseous portion (2), whereby a most external edge (35) of the crown margin (33) of the stump (3) is recessed with respect to a most external edge (26) of the crown margin (24) of the endosseous portion,
    wherein each one of said crown margins (33, 24) is a planar surface, said planar surfaces being not parallel to each other,
    wherein at least one of the crown margins (33, 24) of the endosseous portion or the stump lies on a conical surface while the other one of the crown margins (24, 33) of the endosseous portion or the stump lies on a straight or conical surface having a different taper, so that, once said stump (3) has been coupled to said endosseous portion (2), a contact and interference surface (51) between said crown margins (33, 24) is an annular surface that is smaller compared to a size of the crown margins (33, 24) and proximal to an external edge (35) of said crown margin (33) of said stump (3).

2. The implant (1a, 1b, 1c) for dental prostheses according to claim 1, wherein:
    said crown margin (33) of the stump (3) is conical, lying on the conical surface that widens in an apical direction, so that the external edge (35) of the crown margin (33) is closer to an apical end of the implant than an internal edge (36) thereof;
    said crown margin (24) of the endosseous portion (2) has an opposite taper with respect to a taper of said crown margin (33) of the stump (3) lying on the conical surface that widens in a coronal direction, so that an external edge (26) of the crown margin (24) of the endosseous portion (2) is closer to a coronal end of the implant than an internal edge (27) thereof, and
    wherein, when said stump (3) is coupled to said endosseous portion (2), the contact and interference surface (51) of the two opposed crown margins (33, 24) is essentially a circular line, near to or coinciding with said external edge (35) of the crown margin (33) of said stump (3).

3. The implant (1a, 1b, 1c) for dental prostheses according to claim 1, wherein:
    said crown margin (33) of the stump (3) is conical, lying on a conical surface that widens in an apical direction, so that the external edge (35) of the crown margin (33) is closer to an apical end of the implant than an internal edge (36);
    said crown margin (24) of the endosseous portion (2) lies on a straight plane, and
    wherein, when said stump (3) is coupled to said endosseous portion (2), the contact and interference surface (52) of the two opposed crown margins (33, 24) is essentially a circular line or band near to or coinciding with said external edge (35) of the crown margin (33) of said stump (3).

4. The implant (1a, 1b, 1c) for dental prostheses according to claim 1, wherein:
    said crown margin (24) of the endosseous portion (2) is conical, lying on a conical surface that widens in a coronal direction, so that an external edge (26) of the crown margin (24) of the endosseous portion (2) is closer to a coronal end of the implant than an internal edge (27) thereof;
    wherein said crown margin (33) of the stump (3) lies on a straight plane, and
    wherein, when said stump (3) is coupled to said endosseous portion (2), the contact and interference surface (53) of the two opposed crown margins (33, 24) is essentially a circular line or band near to or coinciding with said external edge (35) of the crown margin (33) of said stump (3).

5. The implant (1a, 1b, 1c) for dental prostheses according to claim 1,
    wherein said endosseous portion (2) comprises an axial grafting recess (23) of a corresponding grafting appendage (32) of said stump (3), and
    wherein said endosseous portion (2) comprises, in proximity to an opening of said grafting recess (23), an annular projection (25) configured to be inserted in a corresponding annular seat (34) present on said grafting appendage (32) of said stump (3), said annular projection (25) and said annular seat (34) being externally delimited by said crown margins (24, 33).

6. The implant (1a, 1b, 1c) for dental prostheses according to claim 1, wherein said opposed crown margins (33, 24) form a 1-5° angle.

* * * * *